(12) United States Patent
Holbrook

(10) Patent No.: US 10,688,035 B2
(45) Date of Patent: Jun. 23, 2020

(54) PROTECTIVE LIQUID COSMETIC PRIMER

(71) Applicant: Ashley Holbrook, Los Angeles, CA (US)

(72) Inventor: Ashley Holbrook, Los Angeles, CA (US)

(*) Notice: Subject to any disclaimer, the term of this patent is extended or adjusted under 35 U.S.C. 154(b) by 55 days.

(21) Appl. No.: 16/159,685

(22) Filed: Oct. 14, 2018

(65) Prior Publication Data

US 2019/0046430 A1  Feb. 14, 2019

(51) Int. Cl.
| | | |
|---|---|---|
| *A61K 9/20* | (2006.01) | |
| *A61K 8/891* | (2006.01) | |
| *A61Q 1/00* | (2006.01) | |
| *A61K 8/19* | (2006.01) | |
| *A61K 8/67* | (2006.01) | |
| *A61K 8/92* | (2006.01) | |

(52) U.S. Cl.
CPC .............. *A61K 8/891* (2013.01); *A61K 8/19* (2013.01); *A61K 8/678* (2013.01); *A61K 8/922* (2013.01); *A61Q 1/00* (2013.01)

(58) Field of Classification Search
None
See application file for complete search history.

(56) References Cited

U.S. PATENT DOCUMENTS

| 4,980,167 A | 12/1990 | Harashima |
| 8,383,167 B2 | 2/2013 | Corstjens et al. |
| 2008/0159970 A1 | 7/2008 | Willemin |
| 2010/0150853 A1* | 6/2010 | Cassin ............... A61K 8/19 424/59 |
| 2012/0276035 A1* | 11/2012 | Lehman, Jr. ............ A61Q 5/12 424/70.12 |
| 2014/0301965 A1 | 10/2014 | Schroeder |
| 2018/0243206 A1* | 8/2018 | Boland ............... A61K 8/9789 |

FOREIGN PATENT DOCUMENTS

| CN | 1883449 A | 12/2006 |
| CN | 102772310 A | 11/2012 |
| EP | 3242651 A1 | 1/2016 |

OTHER PUBLICATIONS

Hourglass Cosmetics Veil Mineral Primer, ingredients list: https://www.amazon.com/Hourglass-Cosmetics-Veil-Mineral-Primer/dp/B002DW07YW.

* cited by examiner

*Primary Examiner* — Susan T Tran
(74) *Attorney, Agent, or Firm* — Scot Fagerland

(57) ABSTRACT

I disclose a silicone-based liquid cosmetic primer that has utility for protecting skin and makeup. The product is dispensed from a liquid dropper and applied to facial skin before the application of foundation or makeup. It has an extremely high silicone content, 65-99% by weight and preferably 85-95%. The silicone forms a protective layer between the skin and makeup. The silicone barrier formed by this product protects the skin from absorption of irritants and toxins in the cosmetics. Simultaneously, the cosmetic products are protected from oil and sweat for longer-lasting duration. The product also contains small concentrations of Vitamin E, lychee oil, and gold dust.

3 Claims, No Drawings

PROTECTIVE LIQUID COSMETIC PRIMER

FIELD OF THE INVENTION

This invention is in the field of liquid cosmetic compounds based on silicone, particularly cosmetic primers. This invention is also in the field of methods for protecting skin from ingredients found in makeup products and protecting makeup from oil and sweat in the skin.

BACKGROUND OF THE INVENTION

The application of makeup or foundation to the face is often preceded by application of a primer. The primer's main function is to provide a smooth, receptive surface for the makeup, i.e. to fill in lines and pores in the user's face or to make it easier to apply the other products. A primer may come in the form of a powder, cream, or liquid.

A problem with primers is that they do a poor job of protecting either the skin or the makeup. The primers currently on the market are highly absorptive. Makeup products contain long lists of ingredients, most of which are not regulated by the FDA or similar agencies. Primers absorb these ingredients and pass them on to the skin. Many of the primers themselves are heavy in ingredients of unknown safety. These products leave the consumer at a high risk of reaction, irritation, abrasions, allergies, infections, and possibly even skin cancer.

Current primers also suffer a problem of being short-lived and unstable. Sweat and oil from the wearer's skin break cause makeup to run after a few hours. This problem could be due in part to a conflict of interest within the cosmetics industry. Companies sell more makeup when it doesn't last as long, so they have an incentive to make unprotective primer. Makeup users often must take one or more restroom breaks on a night out to reapply makeup that is running, smearing, or wearing off.

The current invention is an improved cosmetic primer, which comes in the form of a liquid. In its best mode of use, it is dispensed from a liquid dropper and applied to the face before application of foundation or makeup. The primer includes a small number of ingredients, all of which are safe for skin contact. This product provides a much higher level of two-way protection than today's existing products. It provides a barrier to absorption, so that the skin is protected from cosmetic ingredients. It also improves the resilience of foundation and makeup in the presence of sweat and oil.

The product achieves its high level of protection with a much higher level of silicone content than the current industry norm.

DESCRIPTION OF RELATED TECHNOLOGY

Makeup primers may be water-based, oil-based, or silicone-based. This invention is a silicone-based primer. The industry standard is to use less than 5% silicone. One typical example is "Veil", a primer produced by Hourglass Cosmetics. The first two ingredients on its list are Zinc Oxide 4.20% and Titanium Dioxide 2.45%. A silicone, cyclopentasiloxane, is third in the ingredients list without a disclosed percentage, which indicates that its silicone content is less than 2.45% (probably less than 1%) according to FDA labeling standards. Chinese patent application CN 102,772,310 is for a foundation primer. This application claims a product that is 1-2 parts of dioxy-silicone oil out of 79-99 parts of total ingredients, i.e. 1-2.5% silicone.

Other silicone-based cosmetic products, especially foundations, also typically use a low to moderate percentage of silicone. The industry standard for foundations is approximately 10-20% silicone, 40-60% water, and 20-50% pigments or other ingredients. For example, EP patent application 3,242,651 (Ricard, assigned to L'Oreal) discloses a foundation comprising 10-25% silicone.

U.S. Pat. No. 8,383,167, "Method for cosmetically treating caspase-14 deficiency", was issued to inventors Hugo Corstjens et al. and assigned to ELC Management LLC. The specification indicates, "The composition may also comprise one or more . . . silicone oils . . . . If present, suggested ranges are from about 0.1 to 60%, preferably from about 0.5 to 45%." This is a higher level of silicone than the industry standard for cosmetic products. However, this patent is not for a makeup primer but for a method of treating caspase-14 deficiency.

U.S. Pat. No. 4,980,167 (Harashima and Yoshida, assigned to Dow Corning) discloses a "cosmetic composition" comprising at least two ingredients. One of the ingredients is a "silicone rubber powder containing 0.5-80 wt % of silicone oil." The specification does not indicate the percentage of this powder within the entire composition. As a maximum, the product must be less than 80% silicone oil. Again, however, this patent does not disclose use as a primer.

Among the many ingredients often included in primers, vitamins and fruit extracts are fairly common. Schroeder and Hentrich, in US patent application 2014/0301965, disclose a "cosmetic cleaning agent" containing a silicone. This patent application provides long lists of other potential ingredients, which include lychee extract and vitamin E. However, the silicone in this publication is of a particular class that does not include dimethicone or cyclopentasiloxane. The silicone in the specification and every claim of the Schroeder patent application is a linear polymer that includes a monomer repeated y times, where y is at least 1. That monomer is not present in dimethicone or cyclopentasiloxane. Furthermore, cyclopentasiloxane is a cyclic molecule. This application does not mention gold.

Chinese patent application 1883449 is another application with very long lists of potential ingredients that are not narrowed down to particular chosen embodiments. The ingredients include silicone (which can be dimethicone), lychee, and vitamin E. The application does not specifically mention cyclopentasiloxane or gold.

DESCRIPTION OF THE INVENTION

This invention is a liquid makeup primer. The product bucks the industry standard and is composed almost entirely of silicone. The preferred range is 85-95% silicone; 65-99% is an acceptable window. The silicone may be dimethicone, cyclopentasiloxane, or any combination of these two forms.

The product uses only three other ingredients: lychee oil, vitamin E, and gold dust. Lychee oil has therapeutic and cosmetic value as an anti-oxidant and skin protectant. Vitamin E is effective for soothing the skin in the presence of irritants or desiccants. Gold has underappreciated therapeutic utility as well as its cosmetic value in adding a glittery appearance to the skin. Gold dust enhances a product's marketability as well by making it more visually appealing to shoppers.

I also disclose two methods of using the product. The first is protection of makeup from running and smearing. Tests have shown that makeup lasts hours longer when the wearer uses this product than over-the-counter alternatives. Therefore, one method of use for this product is the protection of foundation and makeup from sweat and oil. Again, the prior art teaches away from this result. Companies that sell both makeup and primer have a conflict of interest; they sell more makeup if it does not last as long.

The second method of using this product is for protecting the skin from cosmetics. Most foundations, makeup products, and even primers themselves have long lists of ingredients that are unregulated by agencies like the FDA and are not known to be safe. The high content of silicone in this product serves as an effective chemical barrier. The prior art teaches away from this result. Existing liquid primers are highly absorptive. They actively draw cosmetic ingredients into the skin.

Due to the nature of this invention as a composition of matter and/or a method of use, I do not believe that drawings are necessary to understand it.

I claim:

1. A liquid primer for cosmetics, comprising
   95-99% by weight of silicones selected from the group consisting of dimethicone, cyclopentasiloxane, and combination thereof;
   lychee oil,
   vitamin E, and
   gold dust.

2. A method for protecting facial skin from direct contact with cosmetic ingredients, comprising the steps of:
   providing a liquid primer comprising
      95-99% by weight of silicones selected from the group consisting of dimethicone, cyclopentasiloxane, and combination thereof;
      lychee oil, vitamin E, and gold dust; and
   applying the liquid primer to human facial skin.

3. A method for protecting cosmetic products from facial skin secretions, comprising the steps of:
   providing a liquid primer comprising
      95-99% by weight of silicones selected from the group consisting of dimethicone, cyclopentasiloxane, and combination thereof;
      lychee oil, vitamin E, and gold dust; and
   applying the liquid primer to human facial skin.

* * * * *